US00PP34559P2

(12) United States Plant Patent
Rubio-Cabetas

(10) Patent No.: US PP34,559 P2
(45) Date of Patent: Sep. 13, 2022

(54) ALMOND TREE NAMED 'I-3-67'

(50) Latin Name: *Prunus dulcis*
Varietal Denomination: I-3-67

(71) Applicant: Centro de Investigación y Tecnología Agroalimentaria de Aragón, Saragossa (ES)

(72) Inventor: Maria Jose Rubio-Cabetas, Saragossa (ES)

(73) Assignee: Centro de Investigación y Tecnología Agroalimentaria de Aragón, Saragossa (ES)

( * ) Notice: Subject to any disclaimer, the term of this patent is extended or adjusted under 35 U.S.C. 154(b) by 0 days.

(21) Appl. No.: 17/463,671

(22) Filed: Sep. 1, 2021

(51) Int. Cl.
*A01H 5/10* (2018.01)
*A01H 6/74* (2018.01)

(52) U.S. Cl.
USPC ..... Plt./155
CPC ..... *A01H 6/7427* (2018.05)

(58) Field of Classification Search
USPC ..... Plt./155
CPC ..... A01H 6/7427
See application file for complete search history.

*Primary Examiner* — Anne Marie Grunberg
(74) *Attorney, Agent, or Firm* — The Webb Law Firm

(57) ABSTRACT

A new and distinct variety of almond tree that exhibits self-compatibility, high fruit quality, and late flowering.

4 Drawing Sheets

Botanical classification: *Prunus dulcis*.
Varietal denomination: 'I-3-67'.

BACKGROUND OF THE INVENTION

The present invention comprises a new and distinct variety of almond tree (*Prunus dulcis*) having the varietal name 'I-3-67'. The new variety was discovered in 2020 as a result of a planned breeding program conducted in Zaragoza, Spain with the purpose of providing self-compatible almond trees with high fruit quality and late flowering. The new variety is the result of a cross between unpatented *Prunus dulcis* almond trees named 'Felisia' (female parent) and 'Moncayo' (male parent). 'I-3-67' was first asexually reproduced by grafting in 2005 in Zaragoza, Spain and has been reproduced true to type over successive asexual reproductions. The tree architecture of the new variety is similar to its female parent, but the round-ovate fruit shape of 'I-3-67' is distinguishable from the ovate fruit shape of 'Felisia'. The fruits of the new variety are similar to its male parent, but the self-compatible nature of 'I-3-67' is distinguishable from 'Moncayo'. The new variety has not been evaluated under all possible environmental conditions. The phenotype of the new variety may vary with variation in environment without a change in the genotype of the new variety.

Unlike the 'Nonpareil' almond tree (unpatented), 'I-3-67' is self-compatible and the flowers of the new variety bloom approximately 3-5 days later. Further, the following traits distinguish 'I-3-67' as a new and distinct variety from other almond tree varieties known to the breeder:

1. Self-compatibility;
2. High fruit quality; and
3. Late flowering.

DESCRIPTION OF THE DRAWINGS

The accompanying photographic images illustrate the new variety at approximately five years of age, with the colors being as nearly true as is possible with color illustrations of this type.

DESCRIPTION OF THE PLANT

Figure 1:
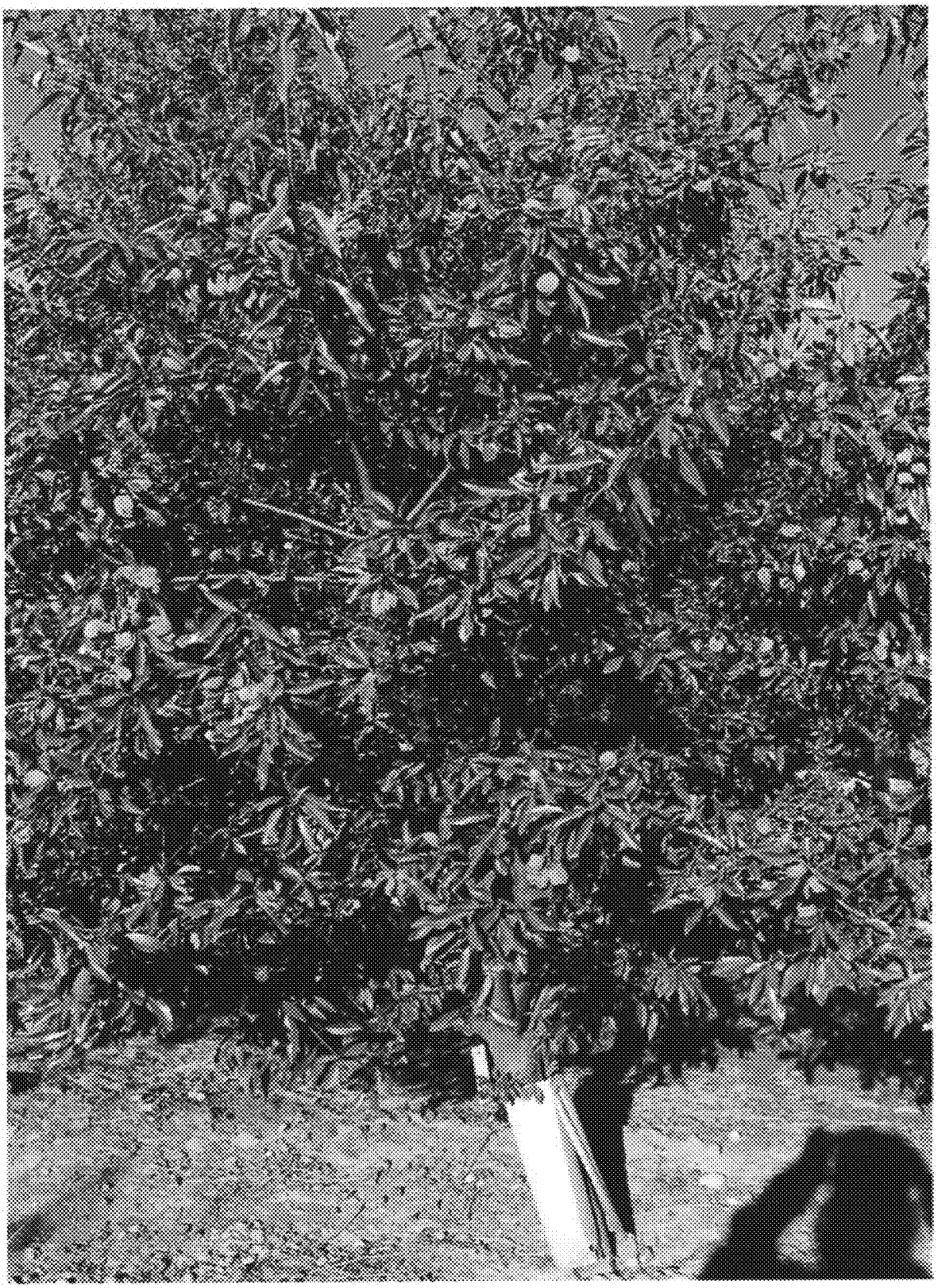
FIG. 1 illustrates a fruiting tree of the new variety.
Figure 2:
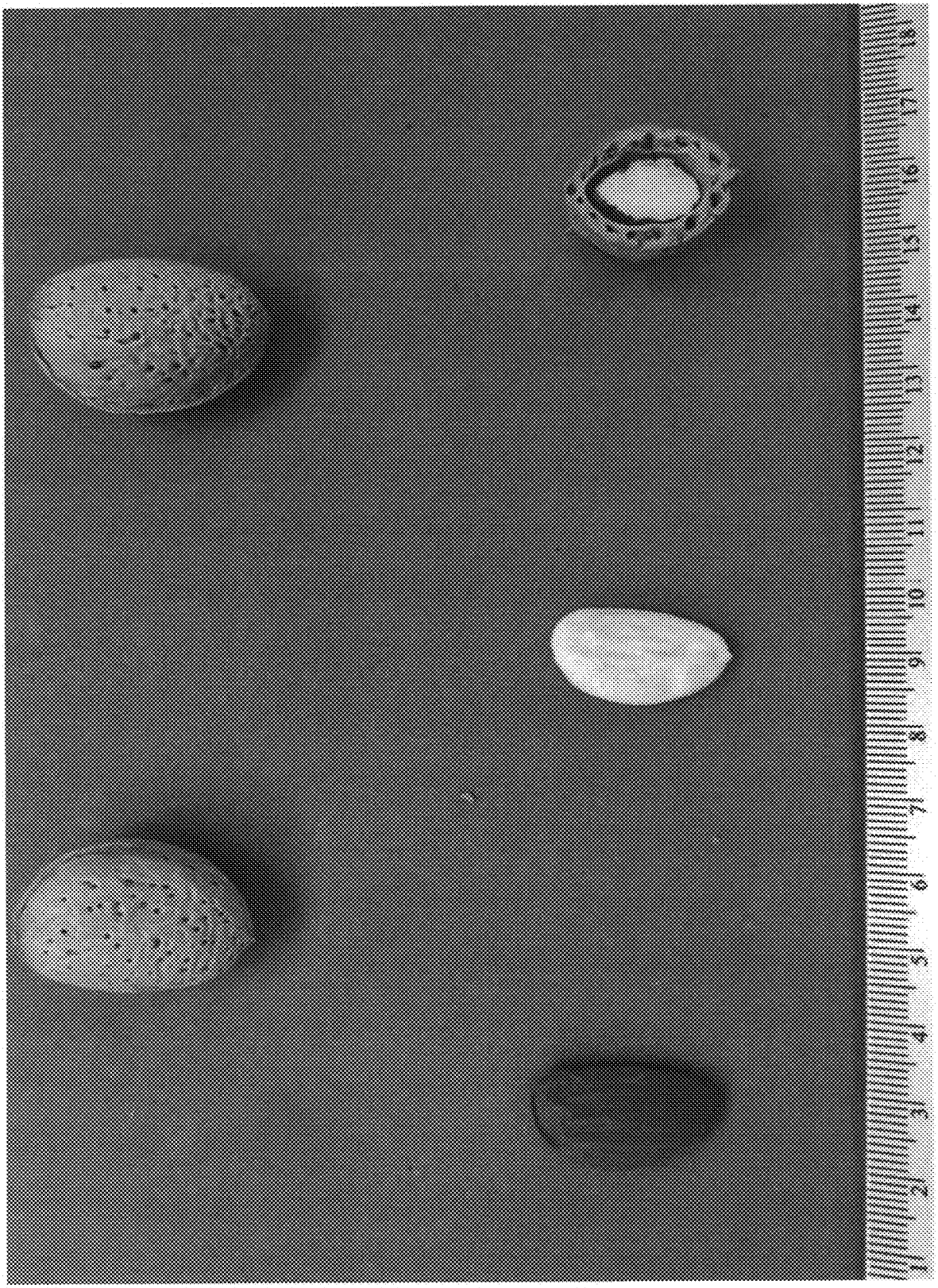
FIG. 2 illustrates the fruits of the new variety.
Figure 3:
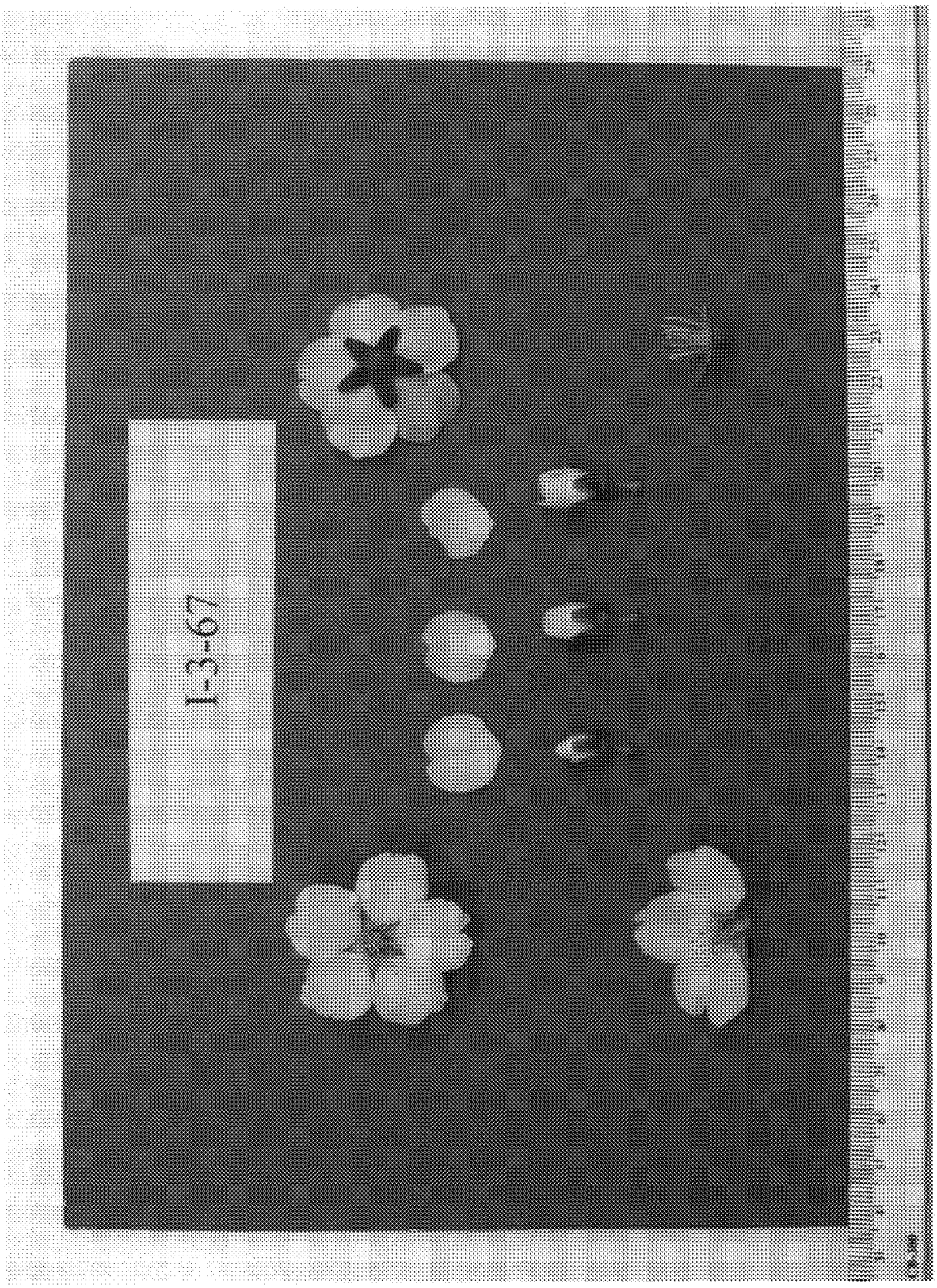
FIG. 3 illustrates the flowers of the new variety.
Figure 4:
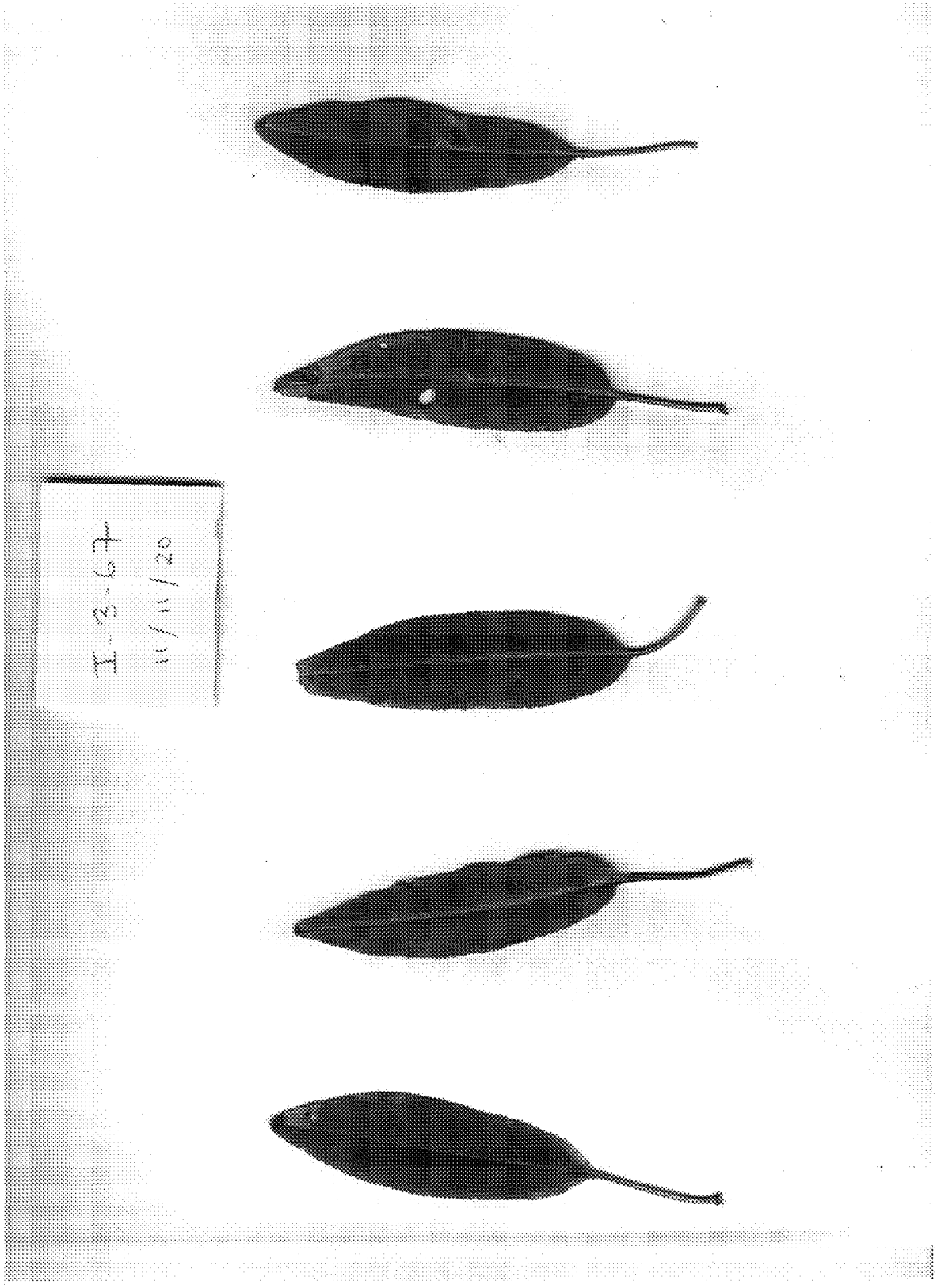
FIG. 4 illustrates the leaves of the new variety.

The following detailed description sets forth the characteristics of the new variety. The color readings and measurements were taken in Zaragoza, Spain under natural light on five year old plants grown in open field conditions, except where other ages are provided. Color references are primarily to The 2015 R.H.S. Colour Chart of The Royal Horticultural Society of London, $6^{th}$ Edition, except where general color terms are used.

PLANT

Overall tree shape: Upright and average.
Height: Low; 2.9 m at 6 years of age.
Spread: Elevated at 6 years of age.
Growth rate: Low.
Habit: Open.
Average time to produce a bearing tree from nursery to planting: Two years.
Disease/pest resistance: None observed.
Cold temperature tolerance: Apparently high, but exact temperature not tested.
Heat tolerance: None observed.
Drought tolerance: None observed.
Trunk:
- *Size.*—Average diameter; 8.42 cm at the midpoint at 6 years of age.
- *Surface texture.*—Rough.
- *Bark color.*—Brownish-red to 177B.
- *Lenticels.*—None observed.

Branches:
- *Number.*—Numerous; an average of 474 per tree.
- *Secondary shoots.*—39 present on current year's shoots.
- *Length.*—0.92 m at one year of age.

*Diameter.*—Small; 13.72 mm at 0.47 m from the branch apex.
*Surface texture.*—Rough.
*Color.*—Brownish-red to 198B.
*Anthocyanin.*—Present on sun exposed area of one year old spurs; 165A in color.
*Form.*—Curved.
*Average angle.*—Open; 65°.
*Bud arrangement.*—Mixed; buds are distributed alternately on each side of the shoot.
*Lenticels.*—None observed.

Leaves:
*Length.*—70.0-80.0 mm.
*Width.*—18.0-25.0 mm.
*Form.*—Moderately elongated.
*Texture.*—Slightly rough.
*Thickness.*—200.0-300.0 μm.
*Base.*—Straight angled.
*Apex.*—Acute.
*Margin.*—Serrate.
*Pubescence.*—None present (both surfaces).
*Color.*—Young leaves: Upper surface: 138A. Lower surface: 138B. Mature leaves: Upper surface: 137C. Lower surface: 137D.
*Glands.*—Number: 2-4. Location: Petiole. Shape: Round. Diameter: 0.25-0.35 mm. Color: 139A (both surfaces).
*Petiole.*—Length: 19.0-29.0 mm. Width: 1.02-1.70 mm. Color: 144D.
*Veins.*—Type: Pinnate. Upper surface color: 144C. Lower surface color: 144D.

Flower buds:
*Pedicel.*—Length: 4.2-5.9 mm. Diameter: 1.0-1.7 mm. Color: 143D.
*Bud.*—Length: 12.3-16.5 mm. Width: 5.8-7.6 mm. Diameter: 31.3-39.3 mm. Shape: Ovate. Color: 60C. Petal tip color: 65D. Sepal color: 60C. Sepal pubescence: Present on hairlines.

Flowers:
*Bloom timing.*—3-5 days after 'Nonpareil'; from February 24$^{th}$ to March 5$^{th}$ in Zaragoza, Spain.
*Pollination requirements.*—None, self-fertile.
*Number.*—Dense; 0.5 per cm.
*Arrangement.*—Mixed; flowers are distributed on both one-year old shoots and spurs, but buds are predominantly on spurs.
*Fragrance.*—Medium intensity.
*Petals.*—Number: 5 per flower. Length: 14.3-16.7 mm. Width: 14.8-16.5 mm. Shape: Broadly heart-shaped. Apex: Cordate. Base: Acute. Margin: Slightly undulate. Texture and appearance: Fine. Color: When opening: Upper surface: NN155D. Lower surface: NN155D. Fully opened: Upper surface: NN155D. Lower surface: NN155D.
*Sepals.*—Shape: Ovate. Margin: Entire. Texture: Pubescent. Length: 4.8-6.5 mm. Width: 3.2-4.2 mm. Color: 60C.

Reproductive organs:
*Stamens.*—Number (per flower): 28-35. Filament length: 7.1-9.5 mm. Filament color: NN155D.
*Anther.*—Shape: Elliptic. Length: 0.80-1.03 mm. Color: 154C. Pollen: Color: 7A. Amount: Abundant.
*Pistil.*—Number (per flower): 1. Length: 9.1-16.7 mm.
*Style.*—Length: 5.1-8.7 mm. Color: 149D.
*Stigma.*—Shape: Rounded. Color: 149C. Ovary color: 149D. Position: Below anthers. Size: 1.0-1.1 mm.

Fruit:
*Average amount of fruit produced per season per non-irrigated tree.*—6.86 kg.
*Time of harvest.*—The first half of September in Zaragoza, Spain.
*Weight.*—Average: 3.86 g. Minimum: 2.78 g. Maximum: 4.53 g.
*Shape.*—Overall: Round-ovate. Apex: Slightly pointed. Base: Straight.
*Height.*—28.78 mm.
*Width.*—23.55 mm.
*Thickness.*—15.04 mm.
*Color.*—Outer surface: Light brown to 164C. Inner surface: Light brown to 164B.
*Surface texture.*—Smooth.
*Resistance to cracking.*—Medium; average.
*Kernel.*—Shape: Ovate. Average weight: 1.041 g. Length: 21.51 mm. Width: 14.83 mm. Apex: Slightly pointed. Base: Straight. Color: Dark brown to 165A. Rugosity: High. Taste: Sweet. Percentage of kernel to fruit: 32.11%.
*Shell/stone.*—Shape: Round-ovate. Length: 21.51 mm. Width: 14.84 mm. Apex shape: Slightly pointed. Color: 164C. Keel size: 1.5 mm. Resistance to cracking: Medium; average.

I claim:

1. A new and distinct variety of almond tree named 'I-3-67', as is herein illustrated and described.

* * * * *